ics(12) United States Patent
Blumich et al.

(10) Patent No.: US 8,242,779 B2
(45) Date of Patent: Aug. 14, 2012

(54) NUCLEAR MAGNETIC RESONANCE METHOD FOR DETECTING HYDROGEN PEROXIDE AND APPARATUS FOR PERFORMING SAID METHOD

(75) Inventors: Bernhard Blumich, Rott (DE); Lisandro Buljabasich Gentiletti, Aachen (DE); Federico Casanova, Aachen (DE); Juan Francisco Perlo, Aachen (DE)

(73) Assignee: RWTH Aachen, Aachen (DE)

( * ) Notice: Subject to any disclaimer, the term of this patent is extended or adjusted under 35 U.S.C. 154(b) by 421 days.

(21) Appl. No.: 12/577,948

(22) Filed: Oct. 13, 2009

(65) Prior Publication Data
US 2010/0090698 A1 Apr. 15, 2010

(30) Foreign Application Priority Data
Oct. 14, 2008 (EP) .................................... 08105570

(51) Int. Cl.
*G01V 3/00* (2006.01)
(52) U.S. Cl. ....................................................... 324/309
(58) Field of Classification Search ........... 324/300–322
See application file for complete search history.

(56) References Cited

U.S. PATENT DOCUMENTS

| 5,270,654 | A | * | 12/1993 | Feinberg et al. | 324/309 |
| 5,541,511 | A | * | 7/1996 | Hennig | 324/309 |
| RE35,656 | E | * | 11/1997 | Feinberg et al. | 324/309 |
| 6,714,009 | B2 | * | 3/2004 | Heidler | 324/303 |
| 7,027,853 | B2 | * | 4/2006 | Ma | 600/410 |
| 7,126,333 | B2 | * | 10/2006 | Beard et al. | 324/303 |
| 7,622,919 | B2 | * | 11/2009 | Song et al. | 324/307 |
| 7,852,077 | B2 | * | 12/2010 | Song et al. | 324/309 |
| 7,898,254 | B2 | * | 3/2011 | Feinberg et al. | 324/309 |

FOREIGN PATENT DOCUMENTS
WO 01/42817 A1 6/2001

OTHER PUBLICATIONS

Stephenson, Ned A., "Quantitative Analysis of Hydrogen Peroxide by 1H NMR Spectroscopy," Analytical and Bioanalytical Chemistry, Springer, Berlin, DE, vol. 381, No. 6, Mar. 1, 2005, pp. 1289-1293, XP019327231, ISSN: 1618-2650 *the whole document*.

(Continued)

*Primary Examiner* — Dixomara Vargas
(74) *Attorney, Agent, or Firm* — BainwoodHuang

(57) ABSTRACT

A nuclear magnetic resonance (NMR) method for detecting hydrogen peroxide includes stimulating a spin signal in a liquid sample in a static magnetic field by exciting the sample with a first electromagnetic pulse having a frequency corresponding to a hydrogen NMR frequency; after a first time period, refocusing the spin signal by a series of second electromagnetic pulses also having the NMR-corresponding frequency and separated by a first echo time, while sampling a first train of spin signals; and refocusing the spin signal by a series of third electromagnetic pulses having the NMR-corresponding frequency and separated by a second echo time while sampling a second train of spin signals, the second echo time different from the first echo time. First and second spin-spin relaxation times are derived from the trains of spin signals, and a quotient of the spin-spin relaxation times indicates the presence of hydrogen peroxide.

18 Claims, 3 Drawing Sheets

OTHER PUBLICATIONS

Anbar, M., et al., "Kinetics of Hydrogen Exchange Between Hydrogen Peroxide and Water Studied by Proton Magnetic Resonance," Journal of the American Chemical Society, Americal Chemical Society, Washington, DC.; US, US, vol. 80, Jun. 5, 1658 (Jun. 5, 1958), pp. 2630-2634, XP007907609, ISSN: 0002-7863 *the whole document*.

Jen et al., "Chemical exchange and nmr T2 relaxation—The multisite case," Journal of Magnetic Resonance, Academic Press, London, GB, vol. 30, No. 1, Apr. 1, 1978, pp. 111-128, XP023959595, ISSN: 0022-2364 [retrieved on Apr. 1, 1978] *the whole document*.

Fullerton, G.D., et al., "NMR relaxation of protons in tissues and other macromolecular water solutions," Magnetic Resonance Imaging, Tarrytown, NY, US, vol. 1, No. 4, Jan. 1, 1982, pp. 209-226, XP023257144, ISSN: 0730-725X [retrieved on Jan. 1, 1982] *the whole document*.

Dobson, C.M., et al., "Measurement of hydrogen exchange rates using 2D NMR spectroscopy," Journal of Magnetic Resonance, Academic Press, London, GB, vol. 69, No. 2, Sep. 1, 1986, pp. 201-209, XP023957266, ISSN: 0022-2364 [retrieved on Sep. 1, 1986] *the whole document*.

* cited by examiner

NUCLEAR MAGNETIC RESONANCE METHOD FOR DETECTING HYDROGEN PEROXIDE AND APPARATUS FOR PERFORMING SAID METHOD

BACKGROUND

The subject matter of the present invention is a method for detecting hydrogen peroxide by means of nuclear magnetic resonance and apparatus for performing said method. The method and apparatus can preferably be used for detecting hydrogen peroxide e.g. in luggage of flight passengers or in parcels or the like.

The detection of explosives or chemical precursors of explosives has an increasing importance due to the increase in terrorist attacks. It is particularly important on airports for checking the luggage of passengers and in freight business for the supervision of parcels. Several techniques, which are e. g. based on X-rays have been tested and implemented in the past. However, in particular X-ray scans of luggage and hand luggage does usually not give any evidence whether a liquid detected is harmless like e. g. water, milk and the like, or whether it is an explosive or a precursor of an explosive like hydrogen peroxide. In the past nuclear magnetic resonance techniques have been tried out. In particular spectroscopic nuclear magnetic resonance techniques, which usually allow a clear distinction of the respective sample, have been tried out. Until now these techniques have been disregarded by the market as the time necessary to perform the respective measurements is quite long and the operative efforts for obtaining a high enough resolution are demanding. Other techniques, like nuclear quadruple resonance (NQR) have been tried out, but they are not applicable for liquid samples. Furthermore, the use of spectroscopic data to detect explosives has been rejected by the market until now due to the high investments to be made mainly for hardware. Furthermore, a spectroscopic database for comparing measurement results with known spectra would be necessary.

Other techniques like dielectric measurements have been tried and implemented. Nevertheless even this fails e. g. for the identification of hydrogen peroxide ($H_2O_2$) from water because both show similar dielectric permitivities.

SUMMARY

Therefore, it is an object of the present invention to provide a technique to overcome the drawbacks known from prior art at least in part and which in particular allows a fast and easy detection of hydrogen peroxide.

This object is solved with the features of the independent claims. Depending claims are directed to improvements of the invention.

The nuclear magnetic resonance (NMR) method for detecting hydrogen peroxide comprises the following steps:
a) providing a liquid sample in a static magnetic field;
b) stimulating a spin-signal in the sample by exciting the sample with a first electromagnetic pulse having a frequency corresponding to the hydrogen-NMR frequency in the static magnetic field;
c) waiting for a first time period;
d) refocusing the spin signal in the sample for a first number of times by a series of second electromagnetic pulses having a frequency corresponding to the hydrogen NMR frequency in the static magnetic field, said second electromagnetic pulses being separated by a first echo time, while sampling a first train of spin signals in between the second electromagnetic pulses;
e) refocusing the spin signal in the sample for a second number of times by a series of third electromagnetic pulses having a frequency corresponding to the hydrogen frequency in the static magnetic field, said third electromagnetic pulses being separated by a second echo time while sampling a second train of spin signals in between the third electromagnetic pulses,
wherein the second echo time is different from the first echo time, wherein a first spin-spin relaxation time is derived from the first train of spin signals and a second spin-spin relaxation time is derived from the second train of spin signals, wherein the presence of hydrogen peroxide is signaled if the quotient of the first spin-spin relaxation time to the second spin-spin relaxation time is different from one.

A spin-signal is stimulated in the sample by irradiating or exciting the sample with an electromagnetic pulse. It is understood that the NMR-frequency is the Larmor frequency of hydrogen in the respective static magnetic field. The term refocusing is understood such, that the spins of the nuclei in the sample are excited by an electromagnetic pulse in such a way that an echo of the spin signal is generated and can be detected. The term spin-spin relaxation is denominated as transverse relaxation as well. The spin-spin relaxation describes the dephasing of the net magnetization of the spins caused by fluctuations of the local magnetic field due to neighbor spins which change the NMR-frequency at the particular position of each spin.

By use of a so called CPMG (Can Purcell Meiboom Gill) pulse sequence with several second and third electromagnetic pulses having different echo times it is possible to measure two spin-spin relaxation times for different echo times in a single train. From the quotient of these two echo times it is possible to deduce whether hydrogen peroxide is present in the sample. If water and hydrogen peroxide are present in the sample, a so called fast chemical exchange takes place between protons in water and in hydrogen peroxide. This results in a significant change of the spin-spin relaxation time which also depends on the echo time used to sample the signal decay. It is preferred in this context to have a second echo time being larger than the first echo time. It is furthermore preferred that the first echo time is significantly smaller than the second echo time.

The first number and the second number of times are preferably adjusted such that the signal amplitude for the last echo sampled after the last pulse of the first number of second electromagnetic pulses is large enough to allow a reasonable detection accuracy with respect to signal to noise during the application of the second number of third electromagnetic pulses. Preferably, the first number and second number are set to get a decay of about two during each train. In a preferred embodiment it is possible to set the first number and second number such that the decay factor of the respective signal trains is the same and is in particular only differing to at most 10%. Alternatively, the first and second number can be set such that these decay factors are different.

According to an improvement of the present invention the presence of hydrogen peroxide is signaled if the value of the first spin-spin relaxation time to the second spin-spin relaxation time is larger than 1.5

This allows a clear distinction of the presence of hydrogen peroxide, in particular for large relative amounts of hydrogen peroxide. Therefore, in particular samples having high contents of hydrogen peroxide can be detected. Usually, these samples are the most dangerous, as they are highly efficient for the creation of explosives.

According to a further improvement of the method according to the present invention the length of the first electromagnetic pulse is set such that the net magnetization generated by the spins of the sample being excited by the first electromagnetic pulse is turned by 90 degree.

This setting allows a good signal to noise ratio on sampling the echo. It is understood that in particular the length of the first magnetic pulse is adjusted such that a maximum signal is reached.

According to a further improvement of the present invention the length of at least one kind of the following electromagnetic pulses:

a) the second electromagnetic pulses and
b) the third electromagnetic pulses are set such, that the magnetization by the spins of the samples being excited by the first electromagnetic pulse is turned by 180°.

This results in a good refocusing of the spin signals and improves the signal-to-noise ratio. It is understood that in particular the length of the respective pulses is adjusted such that a maximum signal is reached.

According to a further improvement of the present invention the spin signals are sampled during an acquisition time using an RF coil having a dead time, wherein the length of the first echo time or the second echo time is set to be equal to the sum of two times the dead time and the acquisition time.

Therefore, it is possible to refocus either the first train of spin signals or the second train of spin signals as fast as possible. This results in a significant difference between respective first or second spin-spin relaxation time and the remaining spin-spin relaxation time and thus allows a more accurate detection of the presence of hydrogen peroxide in the liquid sample. Furthermore, the signal decay due to other processes like e. g. spin-spin relaxation or self-diffusion is diminished.

According to a further improvement of the present invention the first echo time or the second echo time is set to such a value that fast chemical exchange between protons and water and hydrogen peroxide results in a significant reduction of the spin-spin relaxation time. This means, that taking into account the specific circumstances of the measurement like e. g. the strength and homogeneity of the static field, the size of the sensitive volume, the specific kind of coil which is used to excite and sample the signals etc. the respective echo times can be set to reach optimal results.

According to a further improvement of the present invention, the presence of hydrogen peroxide is signaled if the quotient of the of the first spin-spin relaxation time to the second spin-spin relaxation time is larger than the quotient of the spin-spin relaxation time of water at the first echo time and the second echo time, which under relatively homogeneous fields is expected to be 1, but can be slightly larger than 1 in the presence of diffusion attenuation.

This allows an easy calibration of the respective limit for the quotient of the first spin-spin relaxation time and the second spin-spin relaxation time. Therefore given a specific hardware to perform the method of the present invention it is possible to calibrate the method by performing experiments with e. g. water and/or with defined solutions of hydrogen peroxide in water.

This allows the setting of the limiting quotient to the values of larger or smaller than 1 depending on the situation.

According to a further aspect of the present invention an apparatus for executing the method according to the present invention is proposed comprising a) a magnet arrangement for creating a static magnetic field in a sample; and
b) a coil for exciting, refocusing and detecting a spin signal in the sample, wherein the apparatus is suitable and determined to perform the method according to the present invention.

The method according to the present invention can be implemented by an apparatus comprising control means, e. g. a computer or a hardware in general, which generates the frequency of the electromagnetic pulses as well as its shape, length and/or amplitude, controls the waiting times as well as the echo times, and detects or acquires the respective spin signals. This is e. g. done by providing a defined time base and sampling rate to a digitizer required to store the respective field measured by the coil.

According to an improvement of the apparatus of the present invention the coil comprises a surface coil.

A surface coil allows the measurement of quite large samples by placing the sample to be measured next to the coil surface.

In general the provided magnetic field is static over time, and can have a reasonable homogeneity. Placing the sample into a magnet or at the surface of a side of a magnet the measurement process can be automatically started. The signaling of the presence of hydrogen peroxide can be performed by several means e. g. it is possible to give an acoustic and/or an optical signal or any signal which is data processable.

According to a further improvement of the apparatus the magnet arrangement comprises a plurality of magnets arranged in a Halbach configuration wherein the sample is insertable in an opening of the magnet arrangement.

BRIEF DESCRIPTION OF THE DRAWINGS

The details and advantages disclosed for the method according to the present invention are transferable to the apparatus according to the present invention and vice versa. Embodiments of the present invention will now be described in detail by way of example only with reference to the accompanying drawings, in which the following is depicted schematically.

DETAILED DESCRIPTION

Figure 1:
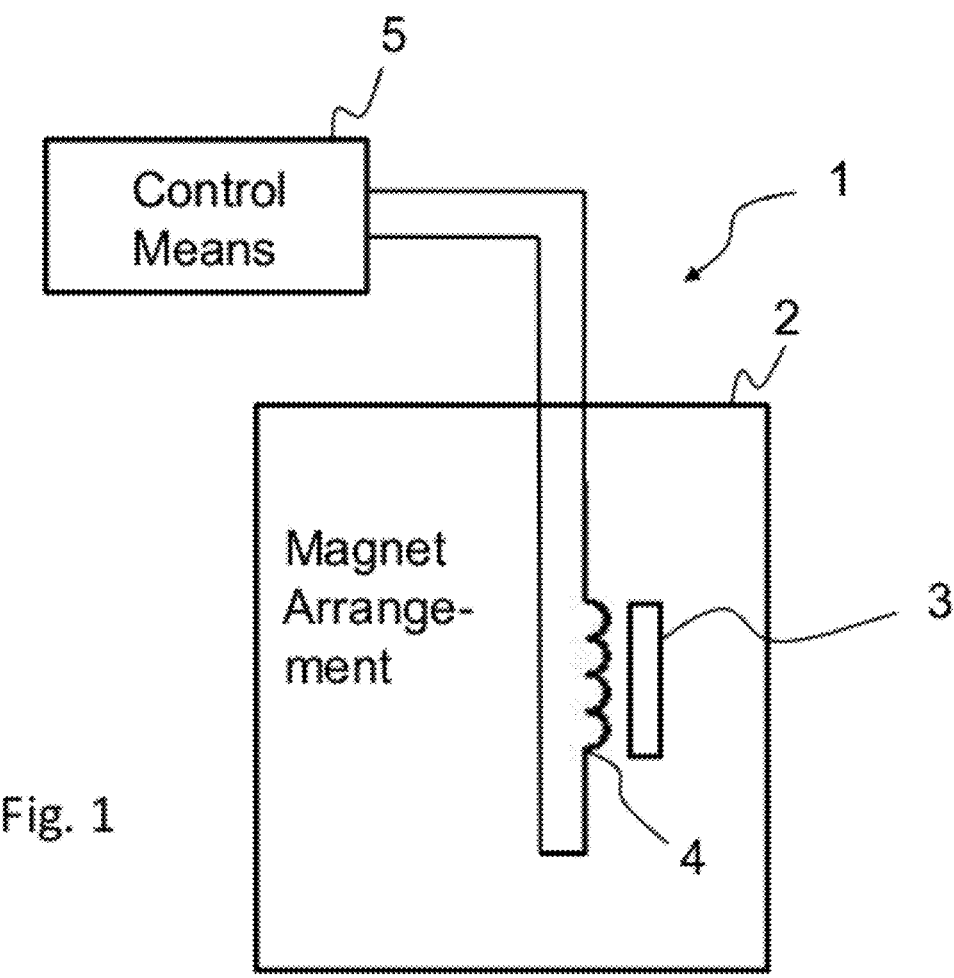
FIG. 1 an embodiment of an apparatus according to the present invention.

FIG. 1 shows schematically an apparatus 1 for executing the method according to the present invention. The apparatus 1 comprises a magnet arrangement 2 for creating a static magnetic field in a sensitive volume to which a sample 3 can be inserted. The magnet arrangement 2 can comprise superconducting magnets, electromagnets, and/or permanent magnets. The magnet arrangement 2 creates a static magnetic field in a sample 3. The apparatus 1 for detecting hydrogen peroxide furthermore comprises a coil 4 for exciting, refocusing and sampling a spin signal in the sample 3. The coil 4 can be a surface coil, a solenoid coil or any other coil that is able to generate and sample the respective magnetic field at the position of the sample 3.

The apparatus 1 for detecting hydrogen peroxide furthermore comprises control means 5. These control means 5 are e. g. included in a computer or the like. The control means 5 are used to generate a signal with a coil 4 at the position of the sample 3. The control means 5 are able to control the frequency, the shape and amplitude of the respective signal.

Furthermore, the control means 5 are able to sample the signal received by the coil 4 after the sample 3 has been excited. The coil 4 is shaped such that the sample 3 is within the so called sensitive volume of the coil 4 in the magnet arrangement 2.

Figure 2:
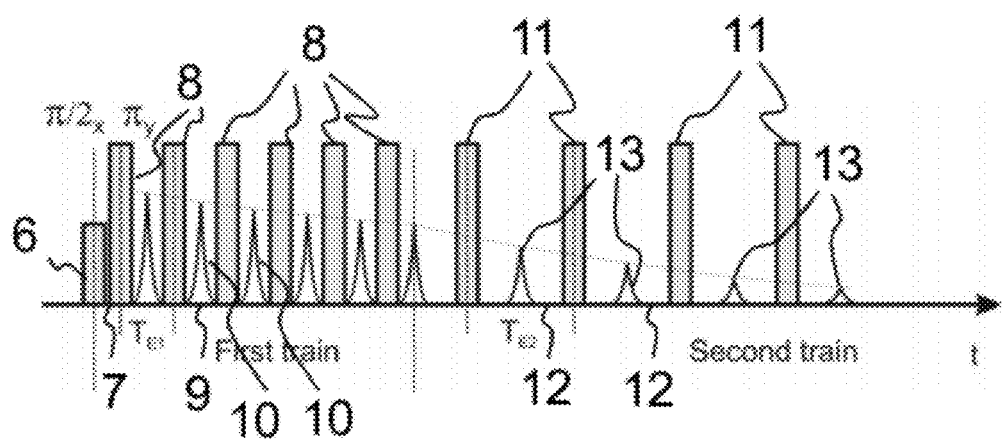
FIG. 2 an example of a method according to the invention.

FIG. 2 depicts schematically an embodiment of the nuclear magnetic resonance (NMR) method for detecting hydrogen peroxide. First of all the liquid sample 3 is provided in the static magnetic field of the magnet arrangement 2. A spin signal is stimulated in the sample 3 by exciting the sample 3 with a first electromagnetic pulse 6 having a frequency corresponding to hydrogen NMR frequency in the static magnetic field of the magnet arrangement 2. After a first time period 7 the spin signal in the sample 3 is refocused for a first number of times by a series of second electromagnetic pulses 8 having a frequency corresponding to hydrogen NMR frequency in the static magnetic field of the magnet arrangement 2. The second electromagnetic pulses 8 are separated by the first echo time 9 and generate the first train 10 of spin signals in between the second electromagnetic pulses 8. The first echo time 9 is denominated $T_{E1}$.

Thereafter, the spin signal of sample 3 is refocused for a second number of times by a series of third electromagnetic pulses 11 having a frequency corresponding to the hydrogen NMR frequency in the static magnetic field of the magnet arrangement 2. The third electromagnetic pulses 11 are separated by a second echo time 12 denominated $T_{E2}$. According to the present invention the second echo time 12 is different from the first echo time 9. A second train 13 of spin signals is sampled in between the third electromagnetic pulses 11. A first spin-spin relaxation time is derived from the first train 10 of spin signals and a second spin-spin relaxation time is derived from the second train 13 of spin signals. This is done e. g. by a suitable fit, in particular a suitable exponential fit to the amplitudes or the intensities of the respective signals of the first 10 and second train 13 of the spin signals. The presence of hydrogen peroxide is signaled if the quotient of the first spin-spin-relaxation time to the second spin-spin relaxation time is different from one.

It is preferred, that the second 8 and the third electromagnetic pulses 11 have the same length and do result therefore in a similar rotation of the net magnetization in the sample 3. For maximizing the signals it is preferred, that the first electromagnetic pulse 6 is so-called a 90°-pulse, whereas the second electromagnetic pulse 8 and the third electromagnetic pulse 11 are so called 180° pulses. The electromagnetic pulses 6, 8, 11 are a so-called Carr-Purcell-Meiboom-Gill (CPMG) pulse sequence. Despite a slight influence of self-diffusion the spin-spin relaxation time $T_2$ is independent of the echo time for usual liquids. This deviates for samples in which fast chemical exchange between hydrogen with different chemical shifts is present. In this case, $T_2$ strongly depends on the echo time.

Chemical exchange takes place, for example, in the protolysis reactions of ammonium ion and of the thrimethyl-substituted ammonium ions in aqueous solution or in samples as N,N-dimethyltrichloroacetamide (DMTCA) and N,N-dimethylcarbamylchloride (TMCC). Furthermore, hydrogenated peroxide in an equilibrium $H_2O_2$/water solution (which is a mixture of $H_2O_2$ and $H_2O$) performs fast exchanges between protons of water and hydrogen peroxide molecules. When being in contact with acetone, in particular if a suitable catalyst is present, hydrogen peroxide reacts with acetone to acetone peroxide, this being an explosive denominated as TATP (triaceton-triperoxide). Furthermore, hydrogen peroxide can be used for generating hexamethylenetriperoxiddi-amine (HMTD).

It was found, that for short echo times the spin-spin relaxation time of a mixture of hydrogen peroxide and water is comparable to the one of pure water. For longer echo times it can be almost one order of magnitude shorter than the spin-spin relaxation time of water. According to the present invention it is possible to sample the spin-spin relaxation time in one measurement (in one shot) for two different echo times in particular one of them set to the shortest possible value taking into account the electronic limitations like e. g. the dead time of the coil and the time necessary for sampling the data in between the second or third electromagnetic pulses 8, 11 and the second one long enough to display an effect of the fast exchange. With this method according to the present invention it is possible to distinguish between hydrogen-peroxide/water solutions and liquids usually expected when e. g. controlling the luggage of flight passengers. Such liquids often comprise water mixtures like wine, apples, creams, fruits, milk or the like, where no fast exchange is present.

Figure 3:
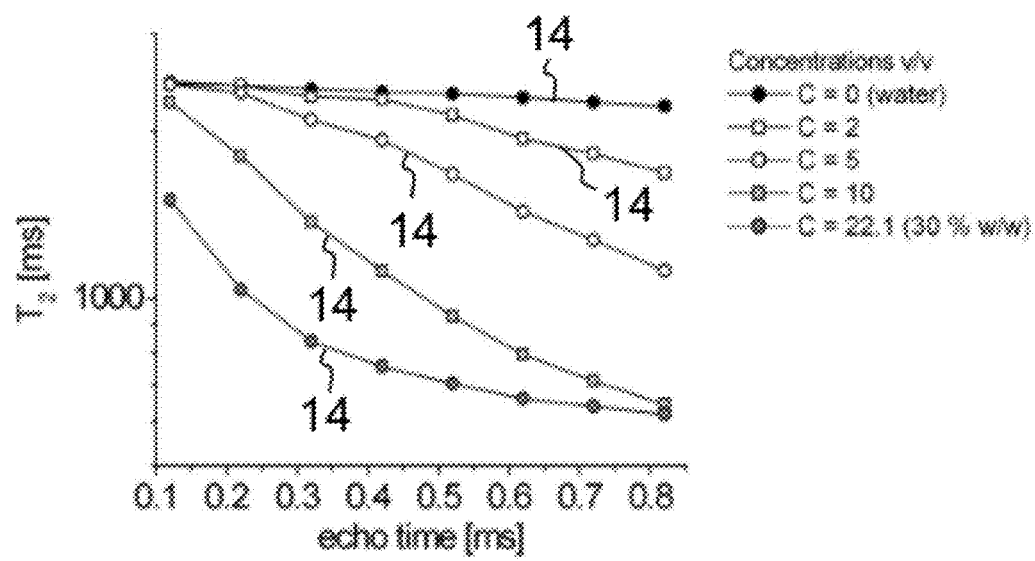
FIG. 3 a first data set of results according to the method of the present invention.

FIG. 3 displays several curves 14 of the spin-spin relaxation time, depending on the echo time of a CPMG sequence depending on the concentration of hydrogen peroxide in water. The inventors found that the behavior of the respective curves 14 changes with the concentration of hydrogen peroxide in a distinguishable manner. That means that the spin-spin relaxation time dependence on the echo time increases with the amount of hydrogen peroxide in the solution. Therefore, with the method according to the present invention it is possible to detect the amount or concentration of hydrogen peroxide in water.

Curves 14 as depicted in FIG. 3 allow a reasonable calibration of the method according to the present invention. For a given magnetic field, the given magnetic field homogeneity and other factors like e.g. sensitive volume and the like it is possible to define a limit for the quotient of the first spin-spin relaxation time to the second spin-spin relaxation time according to the present invention, the exceeding or undercutting of which results in a signalization of the presence of hydrogen peroxide. This means it is e.g. possible to signal the presence of hydrogen peroxide if the concentration of hydrogen peroxide in the solution is higher than two percent.

Figure 4:
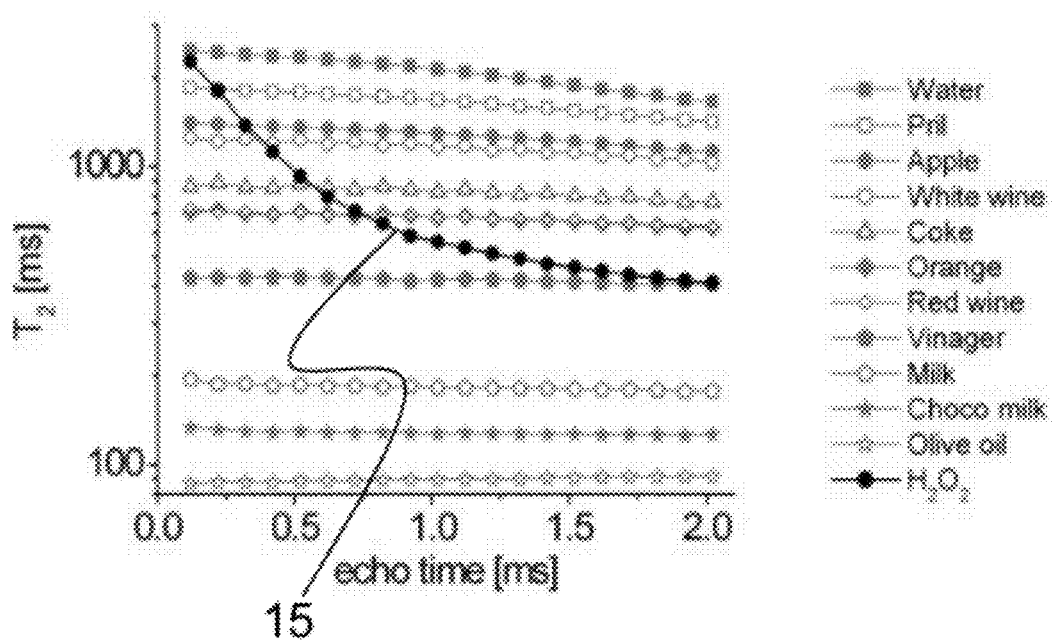
FIG. 4 a second set of results according to the method of the present invention.

FIG. 4 depicts schematically the dependence 15 of the spin-spin relaxation time of a solution of 30 weight-% of hydrogen peroxide in water compared to the spin-spin relaxation time behavior of other samples like e.g. water, wine or the like. It can be seen that if the two echo times TE1 and TE2 are reasonably chosen it is easily possible to discriminate a sample comprising hydrogen peroxide from other samples that might be found in the luggage of flight passengers.

Therefore, the method according to the present invention easily allows the detection of hydrogen peroxide in liquid samples 3 e. g. when controlling luggage or parcels or the like in a very quick way. It takes only seconds to the apparatus to detect and process the signal and indicates the user e. g. with a green/red code or the like the presence of hydrogen peroxide in the sample 3.

Figure 5:
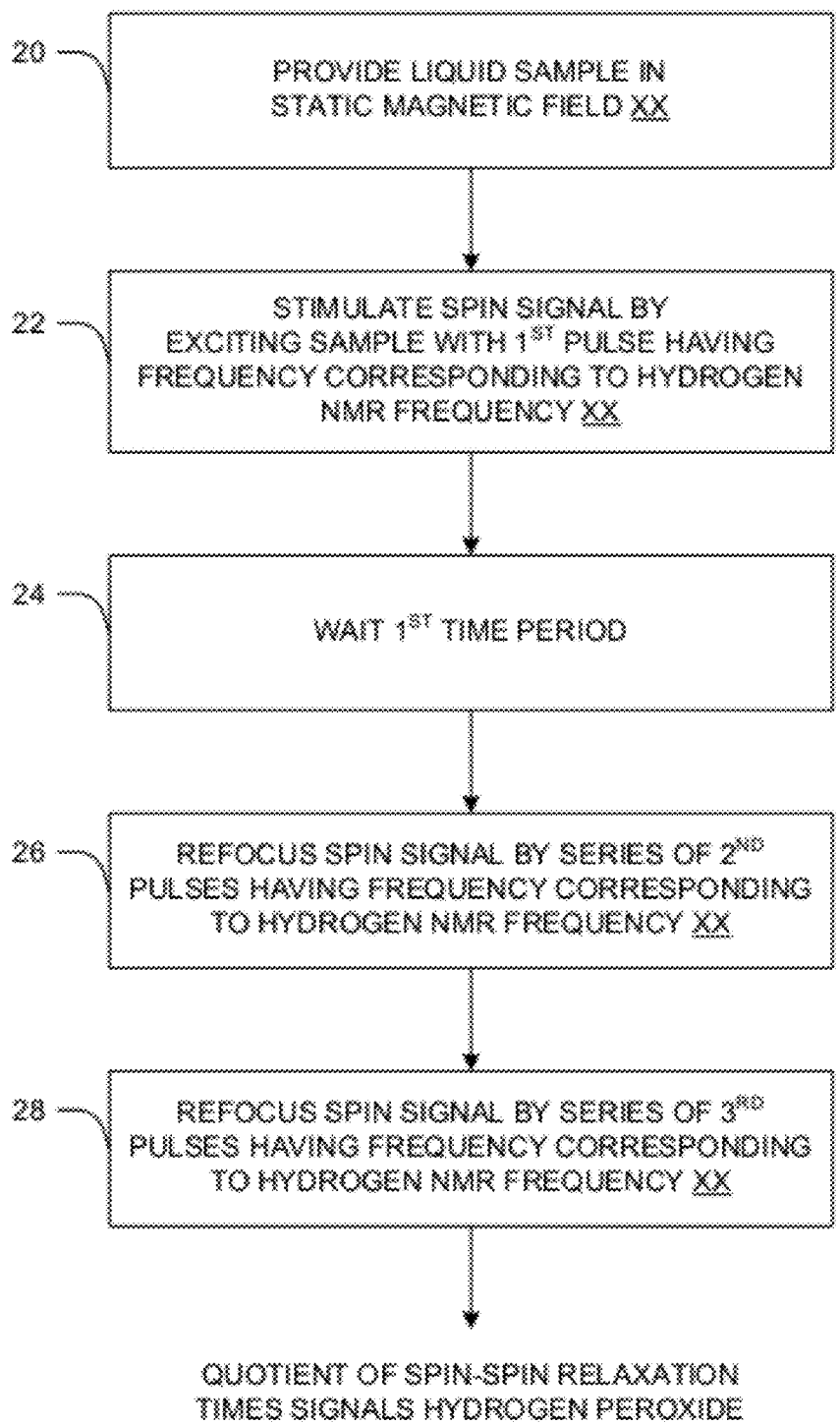
FIG. 5 a flow diagram of a method of the invention.

FIG. 5 shows a nuclear magnetic resonance (NMR) method for detecting hydrogen peroxide. At 20, a liquid sample 3 is provided in a static magnetic field produced by the magnet arrangement 2. At 22, a spin signal is stimulated in the sample by exciting the sample with a first electromagnetic pulse generated by electronic pulse generating circuitry, the first electromagnetic pulse having a frequency corresponding to the hydrogen NMR frequency in the static magnetic field, and at 24 a first time period is waited. At 26, the spin signal is refocused in the sample for a first number of times by a series of second electromagnetic pulses generated by the electronic pulse generating circuitry, each second electromagnetic pulse having a frequency corresponding to the hydrogen NMR frequency in the static magnetic field, said second electromagnetic pulses being separated by a first echo time, while sampling a first train of spin signals in between the second electromagnetic pulses. At 28, the spin signal is refocused in the sample for a second number of times by a series of third electromagnetic pulses generated by the electronic pulse generating circuitry, each third electromagnetic pulse having a frequency corresponding to the hydrogen frequency in the static magnetic field, said third electromagnetic pulses being separated by a second echo time while sampling a second train of spin signals in between the third electromagnetic pulses.

In the process, the second echo time is different from the first echo time. A first spin-spin relaxation time is derived from the first train of spin signals and a second spin-spin relaxation time is derived from the second train of spin signals, and the presence of hydrogen peroxide is signaled if the quotient of the first spin-spin relaxation time to the second spin-spin relaxation time is different from one.

LIST OF REFERENCE NUMBERS

1 apparatus for detecting hydrogen peroxide
2 magnetic arrangement
3 sample
4 coil
5 control means
6 first electromagnetic pulse
7 first time period
8 second electromagnetic pulse
9 first echo time
10 first train of spin signals
11 third electromagnetic pulse
12 second echo time
13 second train of spin signals
14 curve of spin-spin relaxation time of hydrogen peroxide/water mixtures depending on the echo time of a CPMG experiment
15 dependence of the spin-spin relaxation of a hydrogen peroxide/water mixture with a high hydrogen peroxide content

What is claimed is:

1. Nuclear magnetic resonance (NMR) method for detecting hydrogen peroxide, comprising the following steps:
   a) providing a liquid sample in a static magnetic field produced by a magnet arrangement;
   b) stimulating a spin signal in the sample by exciting the sample with a first electromagnetic pulse generated by electronic pulse generating circuitry, the first electromagnetic pulse having a frequency corresponding to the hydrogen NMR frequency in the static magnetic field;
   c) waiting for a first time period;
   d) refocusing the spin signal in the sample for a first number of times by a series of second electromagnetic pulses generated by the electronic pulse generating circuitry, each second electromagnetic pulse having a frequency corresponding to the hydrogen NMR frequency in the static magnetic field, said second electromagnetic pulses being separated by a first echo time, while sampling a first train of spin signals in between the second electromagnetic pulses;
   e) refocusing the spin signal in the sample for a second number of times by a series of third electromagnetic pulses generated by the electronic pulse generating circuitry, each third electromagnetic pulse having a frequency corresponding to the hydrogen frequency in the static magnetic field, said third electromagnetic pulses being separated by a second echo time while sampling a second train of spin signals in between the third electromagnetic pulses,
   wherein the second echo time is different from the first echo time, and wherein a first spin-spin relaxation time is derived from the first train of spin signals and a second spin-spin relaxation time is derived from the second train of spin signals, and wherein the presence of hydrogen peroxide is signaled if the quotient of the first spin-spin relaxation time to the second spin-spin relaxation time is different from one.

2. Method according to claim 1, wherein the presence of hydrogen peroxide is signaled if the quotient of the first spin-spin relaxation time to the second spin-spin relaxation time is larger than 1.5.

3. Method according to claim 1, wherein the length of the first electromagnetic pulse is set such that the net magnetization generated by the spins of the sample being excited by the first electromagnetic pulse is turned by 90°.

4. Method according to claim 1, wherein the length of at least one kind of the following electromagnetic pulses:
   a) the second electromagnetic pulses and
   b) the third electromagnetic pulses
is set such that the net magnetization generated by the spins of the sample being excited by the first electromagnetic pulse is turned by 180°.

5. Method according to claim 1, wherein the spin signals are sampled during an acquisition time using an RF coil having a dead time, wherein the length of the first echo time or the second echo time is set to be equal to the sum of two times the dead time and the acquisition time.

6. Method according to claim 1, wherein the second echo time is set to such a value that fast chemical exchange between protons in water and hydrogen peroxide results in a significant reduction of the spin-spin relaxation time.

7. Method according to claim 1, wherein the presence of hydrogen peroxide is signaled if the quotient of the first spin-spin relaxation time to the second spin-spin relaxation time is larger than the quotient of the spin-spin relaxation times of water at the first echo time and the second echo time.

8. Method according to claim 1, further comprising:
   calculating the quotient of the first spin-spin relaxation time to the second spin-spin relaxation time; and
   comparing the quotient with a limit value greater than one.

9. Apparatus for nuclear magnetic resonance (NMR) detection of hydrogen peroxide, comprising:
   a) a magnet arrangement for creating a static magnetic field in a sample;
   b) a coil for exciting, refocusing and detecting a spin signal in the sample; and
   c) a controller coupled to the coil and operative to:
      i) stimulate a spin signal in the sample via the coil by exciting the sample with a first electromagnetic pulse having a frequency corresponding to the hydrogen NMR frequency in the static magnetic field;
      ii) wait for a first time period;
      iii) refocus the spin signal in the sample via the coil for a first number of times by a series of second electromagnetic pulses having a frequency corresponding to the hydrogen NMR frequency in the static magnetic field, said second electromagnetic pulses being separated by a first echo time, while sampling a first train of spin signals in between the second electromagnetic pulses; and
      iv) refocus the spin signal in the sample via the coil for a second number of times by a series of third electromagnetic pulses having a frequency corresponding to the hydrogen frequency in the static magnetic field, said third electromagnetic pulses being separated by a second echo time while sampling a second train of spin signals in between the third electromagnetic pulses, wherein the second echo time is different from the first echo time, and wherein a first spin-spin relaxation time is derived from the first train of spin signals and a second spin-spin relaxation time is derived from the second train of spin signals, and wherein the presence of hydrogen peroxide is signaled if the quotient of the first spin-spin relaxation time to the second spin-spin relaxation time is different from one.

10. Apparatus according to claim 9, wherein the coil comprises a surface coil.

11. Apparatus according to claim 9, wherein the magnet arrangement comprises a plurality of magnets arranged in a Halbach configuration, and wherein the sample is insertable in an opening of the magnet arrangement.

12. Apparatus according to claim 9, wherein the presence of hydrogen peroxide is signaled if the quotient of the first spin-spin relaxation time to the second spin-spin relaxation time is larger than 1.5.

13. Apparatus according to claim 9, wherein the length of the first electromagnetic pulse is set such that the net magnetization generated by the spins of the sample being ex-cited by the first electromagnetic pulse is turned by 90°.

14. Apparatus according to claim 9, wherein the length of at least one kind of the following electromagnetic pulses:
 a) the second electromagnetic pulses and
 b) the third electromagnetic pulses is set such that the net magnetization generated by the spins of the sample being excited by the first electromagnetic pulse is turned by 180°.

15. Apparatus according to claim 9, wherein the spin signals are sampled during an acquisition time using an RF coil having a dead time, wherein the length of the first echo time or the second echo time is set to be equal to the sum of two times the dead time and the acquisition time.

16. Apparatus according to claim 9, wherein the second echo time is set to such a value that fast chemical exchange between protons in water and hydrogen peroxide results in a significant reduction of the spin-spin relaxation time.

17. Apparatus according to claim 9, wherein the presence of hydrogen peroxide is signaled if the quotient of the first spin-spin relaxation time to the second spin-spin relaxation time is larger than the quotient of the spin-spin relaxation times of water at the first echo time and the second echo time.

18. Apparatus according to claim 9, wherein the controller is further operative to:
 calculate the quotient of the first spin-spin relaxation time to the second spin-spin relaxation time; and
 compare the quotient with a limit value greater than one.

* * * * *